United States Patent
Li et al.

(10) Patent No.: US 12,391,913 B2
(45) Date of Patent: Aug. 19, 2025

(54) LACTIPLANTIBACILLUS PLANTARUM STRAIN FOR ALLEVIATING HYPERURICEMIA AND COMBINATION AND USE THEREOF

(71) Applicant: Northeast Agricultural University, Heilongjiang (CN)

(72) Inventors: Bailiang Li, Heilongjiang (CN); Zhongjiang Wang, Heilongjiang (CN); Zengbo Wang, Heilongjiang (CN); Zengwang Guo, Heilongjiang (CN); Qingxue Chen, Heilongjiang (CN)

(73) Assignee: Northeast Agricultural University, Heilongjiang (CN)

(*) Notice: Subject to any disclaimer, the term of this patent is extended or adjusted under 35 U.S.C. 154(b) by 0 days.

(21) Appl. No.: 18/717,423

(22) PCT Filed: Dec. 5, 2023

(86) PCT No.: PCT/CN2023/136303
§ 371 (c)(1),
(2) Date: Jun. 7, 2024

(87) PCT Pub. No.: WO2024/193100
PCT Pub. Date: Sep. 26, 2024

(65) Prior Publication Data
US 2025/0109375 A1 Apr. 3, 2025

(30) Foreign Application Priority Data
Mar. 22, 2023 (CN) .................. 202310288894.8

(51) Int. Cl.
*C12N 1/20* (2006.01)
*A61K 35/00* (2006.01)
(Continued)

(52) U.S. Cl.
CPC ............ *C12N 1/205* (2021.05); *A61K 35/741* (2013.01); *A61P 19/06* (2018.01); *A61K 2035/115* (2013.01); *C12R 2001/01* (2021.05)

(58) Field of Classification Search
CPC ................. C12N 1/205; A61K 35/741; A61K 2035/115; A61P 19/06; C12R 2001/01
See application file for complete search history.

(56) References Cited

U.S. PATENT DOCUMENTS
2018/0318364 A1 11/2018 O'Hara

FOREIGN PATENT DOCUMENTS
| CN | 110055199 | 7/2019 |
| CN | 115191607 | 10/2022 |

(Continued)

OTHER PUBLICATIONS

English translation of CN115191607 (Year: 2022).*

(Continued)

*Primary Examiner* — Robert B Mondesi
*Assistant Examiner* — Naghmeh Nina Moazzami
(74) *Attorney, Agent, or Firm* — Cooper Legal Group, LLC (57) ABSTRACT

The present disclosure provides a *Lactiplantibacillus plantarum* strain for alleviating hyperuricemia and a combination and use thereof, and belongs to the technical field of microorganisms. The *Lactiplantibacillus plantarum* strain was deposited in the China Center for Type Culture Collection (CCTCC), Wuhan, China on Oct. 19, 2022, with an accession number of CCTCC NO: M20221596. The combination includes the *Lactiplantibacillus plantarum* strain BL-17, 0.01 wt % of a galacto-oligosaccharide, 0.01 wt % of an adenylic acid, and the balance of a sterilized skimmed milk solution. The combination according to the present disclosure can effectively alleviate the high serum uric acid (Continued)

levels in hyperuricemic rats, increase the urine uric acid levels in hyperuricemic rats, reduce the serum creatinine levels in hyperuricemic rats, reduce the serum urea nitrogen levels in hyperuricemic rats, and inhibit the activity of xanthine oxidase (XOD) in the serum and liver of hyperuricemic rats, and has an effect for alleviating hyperuricemia.

3 Claims, 4 Drawing Sheets

(51) Int. Cl.
*A61K 35/741* (2015.01)
*A61P 19/06* (2006.01)
*C12R 1/01* (2006.01)

(56) References Cited

FOREIGN PATENT DOCUMENTS

| | | |
|---|---|---|
| CN | 116286534 | 6/2023 |
| JP | 2013048636 | 3/2013 |

OTHER PUBLICATIONS

Ting Ding et al., "Promoting Effect and Mechanism of Exogenous Nucleotides on the Growth of Lactobacillus casei Q1", Food Science, Nov. 30, 2021, with English abstract, pp. 201-207, vol. 42, No. 22.

"International Search Report (Form PCT/ISA/210) of PCT/CN2023/136303", mailed on Mar. 11, 2024, pp. 1-3.

* cited by examiner

LACTIPLANTIBACILLUS PLANTARUM STRAIN FOR ALLEVIATING HYPERURICEMIA AND COMBINATION AND USE THEREOF

CROSS-REFERENCE TO RELATED APPLICATION

This application is a 371 of international application of PCT application serial no. PCT/CN2023/136303, filed on Dec. 5, 2023, which claims the priority benefit of China application no. 202310288894.8, filed on Mar. 22, 2023. The entirety of each of the above-mentioned patent applications is hereby incorporated by reference herein and made a part of this specification.

TECHNICAL FIELD

The present disclosure relates to a *Lactiplantibacillus plantarum* strain for alleviating hyperuricemia and a combination and a use thereof, and in particular relates to a use of a probiotic/prebiotic combination for alleviating hyperuricemia. The present disclosure belongs to the technical field of microorganisms.

BACKGROUND OF RELATED ART

Uric acid is an end product of purine metabolism in humans, and it is well-known that the elevated serum uric acid level will cause gout and hyperuricemia. The intake of foods high in purines is associated with the elevated serum uric acid level. Nucleic acids in foods such as vegetables are mainly composed of adenine and guanine, and therefore these foods have little impact on the development of hyperuricemia. In contrast, meat from animals, fishes, and some shrimps contains a large amount of hypoxanthine, and the high intake of these foods is associated with the elevated serum uric acid level. The elevated serum uric acid level can be prevented by reducing the absorption of inosine and inosine-related purine compounds (such as hypoxanthine and inosine 5'-monophosphate (IMP)), rather than adenosine and adenosine-related purine compounds.

One strategy aimed at reducing the intestinal absorption of food-derived purines is to consume foods low in purines. Another strategy is to consume foods that can lower the serum uric acid level, which just like drugs such as allopurinol for inhibiting the activity of xanthine oxidase (XOD) in the liver. However, the palatability of foods low in purines is significantly deteriorated because palatable foods often contain high levels of purines, such as umami components. Therefore, the design of a product should consider the impact on food flavor not only in terms of low levels of purines, but also in terms of agents for long-term complete nutrition. Yet another effective strategy is to introduce *Lactobacillus* sp. into a food composition. For example, *Lactobacillus* sp. produces lactic acid as a major metabolic end product during carbohydrate fermentation. The oral ingestion of *Lactobacillus* sp. by a host may have beneficial effects on the host by, for example, activating immune responses. *Lactobacillus* sp. ingested with foods may absorb purines in the intestinal tract of the host, thereby reducing the absorption of purines by the host. However, the existing *Lactobacillus* spp. exhibit insignificant treatment or alleviation effects, and need to be used in combination with a drug for treating or alleviating hyperuricemia. In the treatment of a disease caused by hyperuricemia, the efficacy of a commonly used drug, such as benzbromarone and allopurinol, is limited by drug dosage, drug intolerance, drug-drug interactions, and high toxic and side effects. The above conditions all make the uric acid-lowering treatment more difficult. Therefore, the development of novel high-efficiency and low-toxicity uric acid-lowering drugs is very important for the treatment of hyperuricemia-associated diseases in modern humans. The present disclosure focuses on these factors effectively affecting hyperuricemia and designs a suitable probiotic/prebiotic combination for alleviating hyperuricemia.

SUMMARY OF THE INVENTION

The technical problem to be solved by the present disclosure is to provide a *Lactiplantibacillus plantarum* strain BL-17 for alleviating hyperuricemia.

The present disclosure also provides a combination including the *Lactiplantibacillus plantarum* strain BL-17 for alleviating hyperuricemia.

The present disclosure also provides a preparation method of the combination.

The present disclosure also provides a use of the combination in a preparation of a drug for preventing and/or treating and alleviating hyperuricemia.

The present disclosure also provides a use of the combination in a preparation of a drug for preventing and/or treating gout.

The present disclosure also provides a use of the *Lactiplantibacillus plantarum* strain BL-17 for alleviating hyperuricemia in a preparation of a fermented food.

To solve the above technical problems, the present disclosure adopts the following technical solutions.

A *Lactiplantibacillus plantarum* strain BL-17 for alleviating hyperuricemia is provided, where the *Lactiplantibacillus plantarum* strain BL-17 is deposited in China Center for Type Culture Collection (CCTCC), Wuhan, China on Oct. 19, 2022, with an accession number of CCTCC NO: M20221596.

A combination including the *Lactiplantibacillus plantarum* strain BL-17 for alleviating hyperuricemia is provided, where the combination includes the *Lactiplantibacillus plantarum* strain BL-17 at a viable bacterial cell concentration of higher than or equal to $1 \times 10^6$ CFU/mL or higher than or equal to $1 \times 10^6$ CFU/g, 0.01 wt % of a galacto-oligosaccharide, 0.01 wt % of an adenylic acid, and the balance of a sterilized skimmed milk solution.

The combination includes, but is not limited to, a viable strain, a dried strain, a strain metabolite, or an inactivated strain of the *Lactiplantibacillus plantarum* strain BL-17.

A preparation method of the combination is provided, including the following steps:

step 1, activating the *Lactiplantibacillus plantarum* strain BL-17: streaking the *Lactiplantibacillus plantarum* strain BL-17 on a De Man-Rogosa-Sharpe (MRS) solid medium (formula: peptone: 5.0 g, tryptone: 10.0 g, sodium acetate: 5.0 g, a yeast extract: 5.0 g, glucose: 20.0 g, Tween-80:1.0 g, manganese sulfate: 0.25 g, diammonium hydrogen citrate: 2.0 g, magnesium sulfate: 0.58 g, dipotassium phosphate: 2.0 g, a beef extract: 5.0 g, and an agar: 16.0 g, which are mixed and made up to 1 L with distilled water, then adjusted to a pH of 5.8, and sterilized at 121° C. for 15 min) on a plate, picking a single colony for Gram staining, and after a single pure colony of the *Lactiplantibacillus plantarum* strain BL-17 is observed microscopically, passaging the *Lactiplantibacillus plantarum* strain BL-17 twice in an MRS liquid medium (formula:

peptone: 5.0 g, tryptone: 10.0 g, sodium acetate: 5.0 g, a yeast extract: 5.0 g, glucose: 20.0 g, Tween-80:1.0 g, manganese sulfate: 0.25 g, diammonium hydrogen citrate: 2.0 g, magnesium sulfate: 0.58 g, dipotassium phosphate: 2.0 g, and a beef extract: 5.0 g, which are mixed and made up to 1 L with distilled water, then adjusted to a pH of 5.8, and sterilized at 121° C. for 15 min) until a bacterial viability of the *Lactiplantibacillus plantarum* strain BL-17 is restored to obtain an MRS liquid culture including the *Lactiplantibacillus plantarum* strain BL-17, and finally mixing 50% glycerin and the MRS liquid culture in a volume ratio of 2:3 to obtain a resulting mixture, and storing the resulting mixture at −80° C. for later use;

step 2, inoculating the cryopreserved *Lactiplantibacillus plantarum* strain BL-17 into 5 mL of an MRS liquid medium at an inoculum size of 4% to obtain a mixture, incubating the mixture at 37° C. for 20 hours, followed by activating for two generations to obtain an MRS liquid culture including an activated second-generation *Lactiplantibacillus plantarum* strain BL-17; and centrifuging the MRS liquid culture including the activated second-generation *Lactiplantibacillus plantarum* strain BL-17 at 4° C. and 6,000 r/min for 5 min to obtain a bacterial pellet, collecting the bacterial pellet, washing the bacterial pellet twice with sterile normal saline to obtain a washed bacterial pellet, and collecting the washed bacterial pellet for subsequent preparation of a bacterial suspension; and step 3, resuspending the washed bacterial pellet in a 100 g/L sterilized skimmed milk solution and performing colony counting by a serial dilution and spread plate method to prepare a bacterial suspension with a concentration of $4.0 \times 10^9$ CFU/mL; and adding the galacto-oligosaccharide and the adenylic acid to the bacterial suspension to allow contents of the galacto-oligosaccharide and the adenylic acid each to be a concentration of 0.1 mg/mL.

A use of the combination in a preparation of a drug for preventing and/or treating and alleviating hyperuricemia is provided.

A use of the combination in a preparation of a drug for preventing and/or treating gout is provided.

A use of the *Lactiplantibacillus plantarum* strain BL-17 for alleviating hyperuricemia in a preparation of a fermented food is provided.

The *Lactiplantibacillus plantarum* strain BL-17 has the following characteristics. According to results from the Gram staining, colonies of the *Lactiplantibacillus plantarum* strain BL-17 are round in morphology, and have slightly undulating and rough edges. After the Gram staining, colonies of the *Lactiplantibacillus plantarum* strain BL-17 are grayish-white, and thus the *Lactiplantibacillus plantarum* strain BL-17 is a typical Gram-positive bacterium. The morphological characteristics of the *Lactiplantibacillus plantarum* strain BL-17 are consistent with those of typical *Lactobacillus* species. After being incubated under anaerobic conditions at a constant temperature of 37° C. in the MRS medium for about 12 h, the *Lactiplantibacillus plantarum* strain BL-17 reaches the late logarithmic phase. Moreover, the *Lactiplantibacillus plantarum* strain BL-17 exhibits a high tolerance to a simulated gastrointestinal fluid.

The present disclosure has the following advantages.
1. In the present disclosure, the *Lactiplantibacillus plantarum* strain BL-17 is a probiotic, and the galacto-oligosaccharide and the adenylic acid are prebiotics. The combination according to the present disclosure can effectively alleviate the high serum uric acid levels in hyperuricemic rats, increase the urine uric acid levels in hyperuricemic rats, reduce the serum creatinine levels in hyperuricemic rats, reduce the serum urea nitrogen levels in hyperuricemic rats, and inhibit the activity of XOD in the serum and liver of hyperuricemic rats, and has an effect for alleviating hyperuricemia. The galacto-oligosaccharide and the adenylic acid merely have a slight effect on the above indicators to some extent. Compared with the *Lactiplantibacillus plantarum* strain BL-17 alone, the combination of the *Lactiplantibacillus plantarum* strain BL-17 with the galacto-oligosaccharide and the adenylic acid can greatly improve the alleviation effect of the *Lactiplantibacillus plantarum* strain BL-17. In addition, in the present disclosure, by orally administering the combination of the *Lactiplantibacillus plantarum* strain BL-17 with the galacto-oligosaccharide and the adenylic acid to rats, it is shown that the combination can effectively reduce the intestinal absorption of the purines in the rats. The combination of the *Lactiplantibacillus plantarum* strain BL-17 with the galacto-oligosaccharide and the adenylic acid according to the present disclosure can be used in the preparation of a drug for alleviating hyperuricemia, and can be used for the daily health care of people with hyperuricemia.
2. The combination according to the present disclosure can effectively reduce the intestinal absorption of purines in rats, thereby playing a role in the prevention and/or treatment and alleviation of hyperuricemia and gout.
3. The combination of the *Lactiplantibacillus plantarum* strain BL-17 with the galacto-oligosaccharide and the adenylic acid can degrade purine nucleosides into purine bases, and the purine bases are not prone to be absorbed by intestinal cells to produce nucleosides. The oral administration of the combination to rats can reduce the intestinal absorption of the purines in the rats.

In the present disclosure, the combination of the *Lactiplantibacillus plantarum* strain BL-17 with the galacto-oligosaccharide and the adenylic acid can degrade purine nucleosides into purine bases, and the purine bases are not prone to be absorbed by intestinal cells to produce nucleosides. It has also been shown in the present disclosure that the combination of the *Lactiplantibacillus plantarum* strain BL-17 with the galacto-oligosaccharide and the adenylic acid can absorb exogenous adenylic acid (adenosine 5'-monophosphate), adenosine, and adenine in vitro. The present disclosure demonstrates that the oral administration of the combination of the *Lactiplantibacillus plantarum* strain BL-17 with the galacto-oligosaccharide and the adenylic acid to rats can reduce the intestinal absorption of the purines in rats.

DETAILED DESCRIPTION OF THE EMBODIMENTS

The present disclosure is further described below with reference to the accompanying drawings.

In the present disclosure, the *Lactiplantibacillus plantarum* strain BL-17 was deposited in the China Center for Type Culture Collection (CCTCC), Wuhan, China on Oct. 19, 2022, with an accession number of CCTCC NO: M20221596. The *Lactiplantibacillus plantarum* strain BL-17 can be purchased by the public from the China Center for Type Culture Collection (CCTCC).

Example 1

The *Lactiplantibacillus plantarum* strain BL-17 was isolated from a naturally-fermented yak yogurt prepared by herders in Gansu Province, China.

The *Lactiplantibacillus plantarum* strain BL-17 for alleviating hyperuricemia was provided, and the *Lactiplantibacillus plantarum* strain BL-17 was deposited in the China Center for Type Culture Collection (CCTCC), Wuhan, China on Oct. 19, 2022, with an accession number of CCTCC NO: M20221596.

A combination including the *Lactiplantibacillus plantarum* strain BL-17 for alleviating hyperuricemia was provided, where the combination included the *Lactiplantibacillus plantarum* strain BL-17 at a viable bacterial cell concentration of higher than or equal to $1 \times 10^6$ CFU/mL or higher than or equal to $1 \times 10^6$ CFU/g, 0.01 wt % of a galacto-oligosaccharide, 0.01 wt % of an adenylic acid, and the balance of a sterilized skimmed milk solution.

A preparation method of the combination was provided, including the following steps.

Step 1: activation of the *Lactiplantibacillus plantarum* strain BL-17: The *Lactiplantibacillus plantarum* strain BL-17 was streaked on an MRS solid medium (formula: peptone: 5.0 g, tryptone: 10.0 g, sodium acetate: 5.0 g, a yeast extract: 5.0 g, glucose: 20.0 g, Tween-80:1.0 g, manganese sulfate: 0.25 g, diammonium hydrogen citrate: 2.0 g, magnesium sulfate: 0.58 g, dipotassium phosphate: 2.0 g, a beef extract: 5.0 g, and an agar: 16.0 g, which were mixed and made up to 1 L with distilled water, then adjusted to a pH of 5.8, and sterilized at 121° C. for 15 min) on a plate. A single colony was picked for Gram staining, and after a single pure colony of the *Lactiplantibacillus plantarum* strain BL-17 was observed microscopically, the *Lactiplantibacillus plantarum* strain BL-17 was passaged twice in an MRS liquid medium (formula: peptone: 5.0 g, tryptone: 10.0 g, sodium acetate: 5.0 g, a yeast extract: 5.0 g, glucose: 20.0 g, Tween-80:1.0 g, manganese sulfate: 0.25 g, diammonium hydrogen citrate: 2.0 g, magnesium sulfate: 0.58 g, dipotassium phosphate: 2.0 g, and a beef extract: 5.0 g, which were mixed and made up to 1 L with distilled water, then adjusted to a pH of 5.8, and sterilized at 121° C. for 15 min) until the bacterial viability of the *Lactiplantibacillus plantarum* strain BL-17 was restored to obtain an MRS liquid culture including the *Lactiplantibacillus plantarum* strain BL-17. Finally, 50% glycerin and the MRS liquid culture were mixed in a volume ratio of 2:3 to obtain a resulting mixture, and the resulting mixture was stored at −80° C. for later use.

Step 2: the cryopreserved *Lactiplantibacillus plantarum* strain BL-17 was inoculated in 5 mL of an MRS liquid medium at an inoculum size of 4%, incubated at 37° C. for 20 hours, and activated for two generations to obtain an MRS liquid culture including an activated second-generation *Lactiplantibacillus plantarum* strain BL-17. The MRS liquid culture including the activated second-generation *Lactiplantibacillus plantarum* strain BL-17 was centrifuged at 4° C. and 6,000 r/min for 5 min to obtain a bacterial pellet. The bacterial pellet was collected and washed twice with sterile normal saline to obtain a washed bacterial pellet, and the washed bacterial pellet was collected for subsequent preparation of a bacterial suspension.

Step 3: the washed bacterial pellet was resuspended in a 100 g/L sterilized skimmed milk solution, and subjected to colony counting by a serial dilution and spread plate method, to prepare a bacterial suspension with a concentration of $4.0 \times 10^9$ CFU/mL. The galacto-oligosaccharide and the adenylic acid were added to the bacterial suspension to allow the contents of the galacto-oligosaccharide and the adenylic acid each to be a concentration of 0.1 mg/mL.

A use of the combination in the preparation of a drug for preventing and/or treating and alleviating hyperuricemia was provided.

A use of the combination in the preparation of a drug for preventing and/or treating gout was provided.

A use of the *Lactiplantibacillus plantarum* strain BL-17 for alleviating hyperuricemia in the preparation of a fermented food was provided.

1. Experimental Animals and Group Design

The animal experiment was divided into three stages: a rat acclimating and grouping stage (one week), a hyperuricemia modeling stage (one week), and a group treatment stage (two weeks). The specific experimental protocol of each stage was as follows.

First Stage (Rat Acclimating and Experimental Grouping):

48 healthy specific pathogen-free (SPF) male Wistar rats (7 weeks, body weight: (200±20) g) were selected. In order to acclimate to a new environment, the 48 male rats were maintained in the animal house with the temperature of 22° C., the humidity of 10% to 60%, and 12 h/12 h light/dark cycle, and fed with standard diet and water ad libitum for 1 week. After the 1 week of acclimating, all experimental rats were randomly assigned to the following 6 groups with 8 rats per group: a control group (group A), a model group (group B), a *Lactiplantibacillus plantarum* strain BL-17 treated group (group C), a galacto-oligosaccharide-adenylic acid treated group (group D), a combination treated group (group E), and an allopurinol intervention treated group (positive control) (group F).

Second Stage (Hyperuricemia Modeling):

Starting from day 8, rats in the control group were intraperitoneally injected with a 0.5% sodium carboxymethyl cellulose (CMC-Na) solution and then subcutaneously injected with a 0.5% CMC-Na solution (the injection volume of the 0.5% CMC-Na solution was the same as the intraperitoneal injection volume of 300.00 mg/kg xanthine/CMC-Na solution and the subcutaneous injection volume of 300.00 mg/kg potassium oxonate/CMC-Na solution), and rats in the 5 groups other than the control group were intraperitoneally injected with the 300.00 mg/kg xanthine/CMC-Na solution (which was prepared by dissolving xanthine in a 0.5% CMC-Na aqueous solution) and then subcutaneously injected with the 300.00 mg/kg potassium oxonate/CMC-Na solution (which was prepared by dissolving potassium oxonate in a 0.5% CMC-Na aqueous solution) to establish the hyperuricemia model.

Third Stage (Group Treatment):

Starting from day 15, rats in drug groups were orally gavaged with corresponding drugs once daily, respectively. Specifically, rats in the control group and the model group were orally gavaged with 10.00 mL/kg normal saline. Rats in the *Lactiplantibacillus plantarum* strain BL-17 treated group were administered with a suspension of *Lactiplantibacillus plantarum* strain BL-17 at $1\times10^9$ CFU/rat. Rats in the galacto-oligosaccharide-adenylic acid treated group were administered with the galacto-oligosaccharide at 10 mg/kg and the adenylic acid at 10 mg/kg, where the galacto-oligosaccharide and the adenylic acid were prepared with a 100 g/L sterilized skimmed milk solution (commercially available) into a solution in which concentrations of the galacto-oligosaccharide and the adenylic acid each were 0.1 mg/mL, and then the rats were orally gavaged with the solution at 10.00 mL/kg. Rats in the combination treated group were orally gavaged with the combination of the *Lactiplantibacillus plantarum* strain BL-17 ($1\times10^9$ CFU/rat) with the galacto-oligosaccharide and the adenylic acid (10 mg/kg), that is, orally gavaged with 10.00 mL/kg the combination. Rats in the allopurinol intervention treated group were orally gavaged with 5 mg/kg allopurinol/CMC-Na solution (which was prepared by dissolving allopurinol in a 0.5% CMC-Na aqueous solution). The group treatment was performed for 14 days.

At the late stage of the experiment, fresh feces of the rats were collected and frozen in a $-80°$ C. refrigerator. At the end of the experiment, the rats were fasted without water deprivation for 12 h and then intraperitoneally injected with a pentobarbital sodium solution at 0.1 mL/10 g for anaesthetization, blood was collected from retro-orbital venous plexuses of rats in each group, then the rats were sacrificed through cervical dislocation, and liver tissues of the rats were collected on ice. The blood sample was centrifuged at 3,500 r/min for 15 min to obtain the supernatant, and the supernatant was collected and frozen at $-80°$ C. for blood indicator analysis. After being collected, the liver tissue was immediately rinsed with pre-cooled normal saline to remove blood, rapidly frozen in liquid nitrogen and then frozen at $-80°$ C., and subsequently homogenized into liver homogenate, and then relevant indicators were determined.

2. Experiments of the Combination to Reduce Serum Uric Acid, Creatinine, and Urea Nitrogen Levels in Hyperuricemic Rats The supernatant of blood sample was taken and added to a 1.5 mL centrifuge tube to obtain a serum sample, and contents of uric acid, creatinine, and urea nitrogen in the serum sample were determined according to determination methods provided by respective assay kits.

Figure 1:
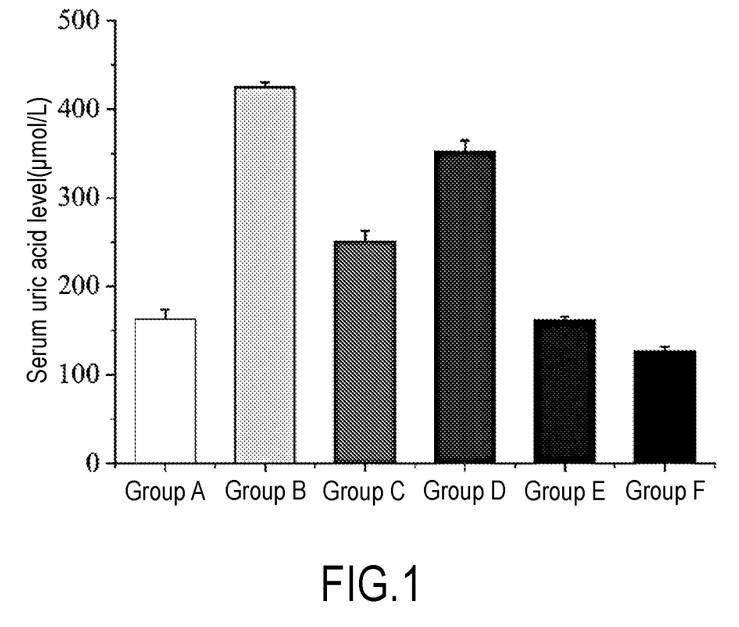
FIG. 1 shows the effect of the combination of the present disclosure on the serum uric acid levels in hyperuricemic rats.

The effect of the combination on serum uric acid levels in rats is shown in FIG. 1. The serum uric acid concentration in the model group (the group B) is (424.33±6.03) μmol/L, which is significantly higher than the serum uric acid concentration in the control group (the group A) ($P<0.01$), indicating that the combination of potassium oxonate and xanthine has a prominent effect for inducing a hyperuricemia model. Compared with the serum uric acid concentration in rats of the model group (the group B), serum uric acid concentrations in rats of the *Lactiplantibacillus plantarum* strain BL-17 treated group (the group C), the galacto-oligosaccharide-adenylic acid treated group (the group D), the combination treated group (the group E), and the allopurinol intervention treated group (the group F) all decrease. There is a limited effect in the galacto-oligosaccharide-adenylic acid treated group (the group D). There is a significant difference between the *Lactiplantibacillus plantarum* strain BL-17 treated group (the group C) and the model group (the group B), and serum uric acid levels in rats of the *Lactiplantibacillus plantarum* strain BL-17 treated group can be adjusted to some extent. The serum uric acid levels in rats of the combination treated group (the group E) are significantly lower than the serum uric acid levels in rats of the model group (the group B) and the *Lactiplantibacillus plantarum* strain BL-17 treated group (the group C), and are close to serum uric acid levels in rats of the allopurinol intervention treated group (the group F) in a practical sense. Compared with serum uric acid levels in rats of the hyperuricemia model group (the group B), serum uric acid levels in hyperuricemic rats of the *Lactiplantibacillus plantarum* strain BL-17 treated group (the group C) are reduced by 40.85%, and serum uric acid levels in hyperuricemic rats of the combination treated group (the group E) are reduced by 62.13%. The uric acid-lowering effect of the combination is similar to the uric acid-lowering effect of the drug allopurinol, which can prevent and reduce the occurrence of hyperuricemia and gout.

Figure 2:
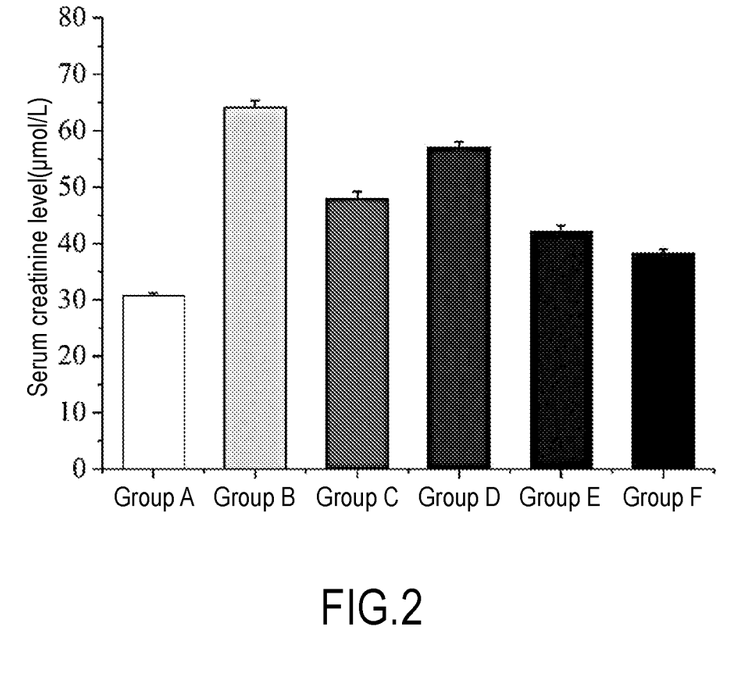
FIG. 2 shows the effect of the combination of the present disclosure on the serum creatinine levels in hyperuricemic rats.

The serum creatinine level is used to evaluate a glomerular filtration rate. Serum uric acid and creatinine levels are higher than normal levels when a renal function is impaired. The effect of the combination on serum creatinine levels in rats is shown in FIG. 2. Compared with serum creatinine levels in rats of the hyperuricemia model group, serum creatinine levels in rats of the *Lactiplantibacillus plantarum* strain BL-17 treated group (the group C), the galacto-oligosaccharide-adenylic acid treated group (the group D), the combination treated group (the group E), and the allopurinol intervention treated group (the group F) all decrease, and serum creatinine levels in hyperuricemic rats of the combination treated group (the group E) decrease by 34.31%. The creatinine-lowering effect of the combination is similar to the creatinine-lowering effect of the drug allopurinol, which can prevent and reduce the occurrence of hyperuricemia and gout.

Figure 3:
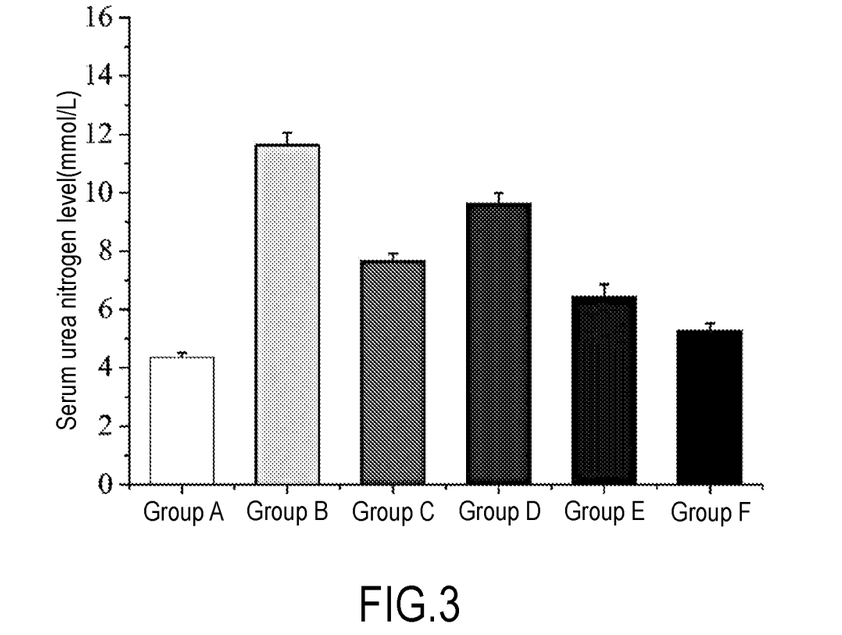
FIG. 3 shows the effect of the combination of the present disclosure on the serum urea nitrogen levels in hyperuricemic rats.

The effect of the combination on a serum urea nitrogen level in rats is shown in FIG. 3, and is similar to the effect of the combination on a serum creatinine level. Compared with serum urea nitrogen levels in rats of the hyperuricemia model group, serum urea nitrogen levels in hyperuricemic rats of the combination treated group (the group E) decrease by 44.88%, indicating that the combination treated group (the group E) has a strong scavenging effect for serum urea nitrogen.

3. An Experiment of the Combination to Adjust an Amount of Uric Acid Excreted by Hyperuricemic Rats The collected urine was diluted with distilled water at 10-fold volume of the collected urine, heated at 50° C. to allow precipitates to be dissolved, and centrifuged at 2,000 r/min for 10 min to obtain a supernatant, and the supernatant was collected and assayed for urinary uric acid level according to a determination method of a uric acid assay kit.

Figure 4:
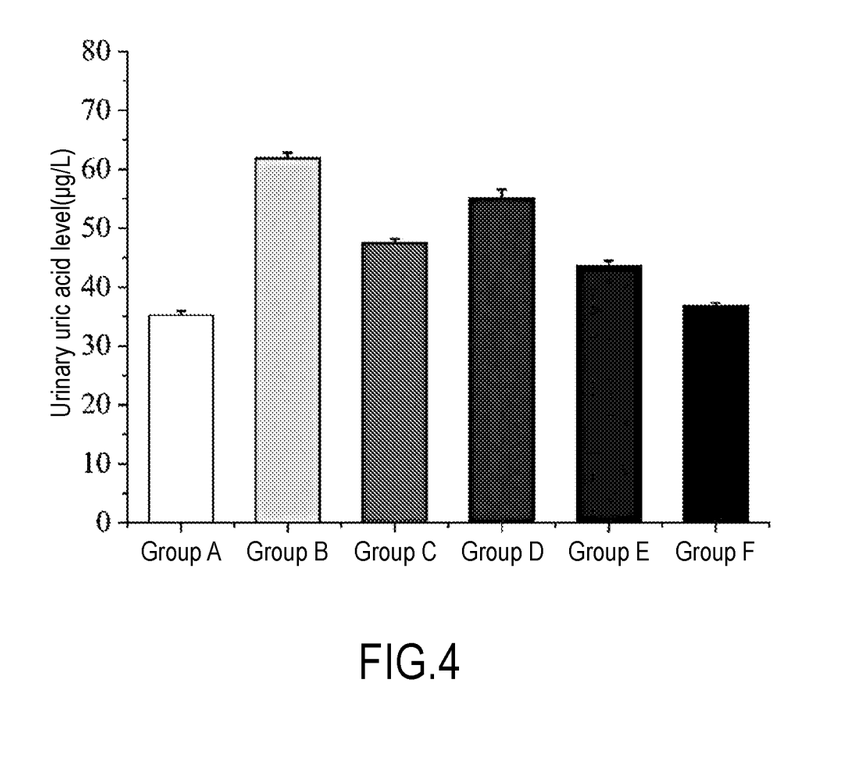
FIG. 4 shows the effect of the combination of the present disclosure on the urine uric acid levels in hyperuricemic rats.

The effect of the combination on a urinary uric acid level in rats is shown in FIG. 4. Compared with urinary uric acid contents in rats of the control group (the group A), urinary uric acid contents in hyperuricemic rats of groups other than the allopurinol intervention treated group (the group F) significantly increase ($P<0.01$). Compared with urinary uric acid levels in rats of the model group (the group B), urinary uric acid levels in rats of the allopurinol intervention treated group (the group F) decrease to urinary uric acid levels in rats of the control group (the group A) and reach urinary uric acid levels in disease-free rats. Urinary uric acid levels in rats of the *Lactiplantibacillus plantarum* strain BL-17 treated group (the group C) and the galacto-oligosaccharide-adenylic acid treated group (the group D) decrease to some extent, and urinary uric acid levels in rats of the combination treated group (the group E) significantly decrease and are close to urinary uric acid levels in rats of the allopurinol intervention treated group (the group F).

4. Experiments of the Combination to Reduce the Activity of XOD in Serum and Liver Tissues of Hyperuricemic Rats Liver tissue was added to 0.9% normal saline according to a weight (mg)/volume (μL) ratio of 1:9 and mechanically homogenized in an ice water bath to obtain a 10% homogenate, the homogenate was centrifuged at 3,000 r/min for 10 min to obtain a supernatant, and the supernatant was collected and assayed for XOD content by enzymatic colorimetry according to instructions of an XOD assay kit. The activity of XOD in serum was also determined by a kit.

Figure 5A:
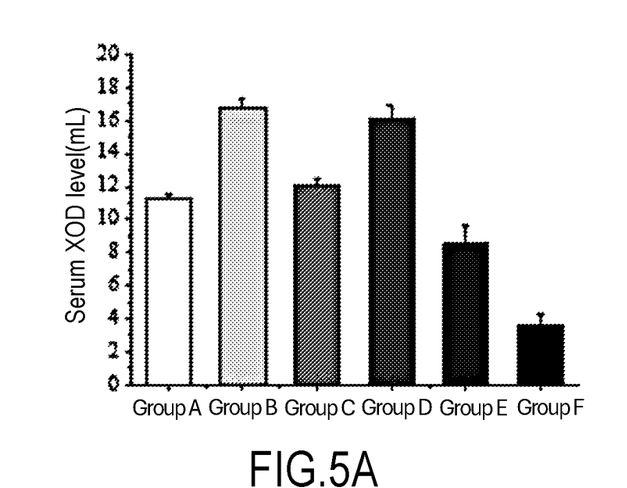
FIG. 5A and FIG. 5B show the effect of the combination of the present disclosure on the activity of XOD in the serum and liver of hyperuricemic rats.
Figure 5B:
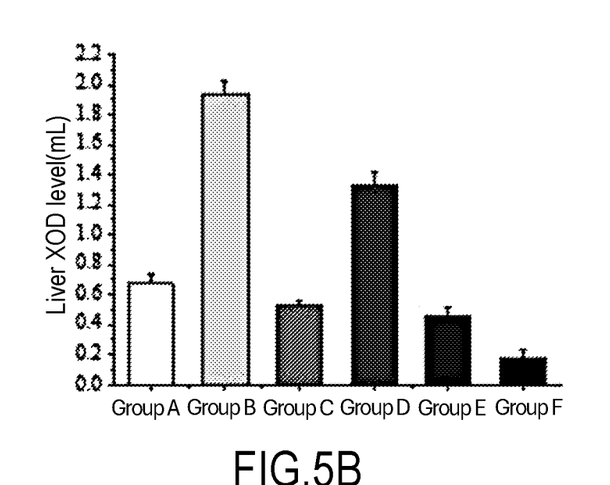

XOD is the key enzyme in purine metabolism to synthesize uric acid. The mechanism by which most existing uric acid-lowering substances exert the uric acid-lowering effect is to effectively inhibit the activity of XOD to reduce the synthesis of uric acid, thereby exerting the uric acid-lowering effect. As shown in FIG. 5A and FIG. 5B, compared with activities of XOD in serum and liver of hyperuricemic rats of the model group, activities of XOD in serum and liver of hyperuricemic rats of the *Lactiplantibacillus plantarum* strain BL-17 treated group (the group C), the galacto-oligosaccharide-adenylic acid treated group (the group D), the combination treated group (the group E), and the allopurinol intervention treated group (the group F) decrease to varying degrees. In particular, activities of XOD in serum and liver of hyperuricemic rats of the *Lactiplantibacillus plantarum* strain BL-17 treated group (the group C) and the combination treated group (the group E) decrease by 49.10% and 76.28%, respectively, such that activities of XOD in the serum and liver of the hyperuricemic rats are close to normal levels, and the synthesis of uric acid in the rats is reduced, which is conducive to the prevention and treatment of hyperuricemia and gout.

As a major regulator organ of uric acid excretion, kidney plays an important role in the uric acid excretion, including glomerular filtration, tubular reabsorption, and secretion. It is reported that about 90% of hyperuricemia cases is mainly caused by insufficient renal uric acid excretion. The combination treated group (the group E) can significantly reduce the serum uric acid, creatinine, and urea nitrogen levels, reduce the urinary uric acid excretion, and inhibit the activity of XOD in the serum and liver in hyperuricemic rats, indicating that the present disclosure has prominent uric acid-lowering and liver and kidney-protecting effects for potassium oxonate and xanthine-induced hyperuricemic rats.

5. Research on a Mechanism of the Combination of the Present Disclosure to Alleviate Hyperuricemia 5.1. Animal Experiment Design Male Wistar rats (8 weeks, body weight: 190 g to 210 g) were selected and maintained in an animal laboratory under controlled environmental conditions: the temperature: 20° C. to 26° C., the relative humidity: 40% to 70%, and a light/dark cycle: 12 h/12 h. All rats were given with a normal diet and tap water for one week. According to body weights, the rats were randomly assigned to a control group (8 rats), a purine treated group (8 rats), and a purine-combination treated group (8 rats). The rats were fasted for 16 h. Rats in the control group each were orally gavaged with 2 mL of normal saline, rats in the purine treated group each were orally gavaged with 10 mL of $^{14}$C-inosinic acid, $^{14}$C-inosine, or $^{14}$C-hypoxanthine at a concentration of 0.5 wt %, and rats in the purine-combination treated group each were orally administered with 10 mL of $^{14}$C-inosinic acid, $^{14}$C-inosine, or $^{14}$C-hypoxanthine at a concentration of 0.5 wt % and 2 mL of the combination. At 0 min, 15 min, 30 min, 45 min, 60 min, 90 min, 120 min, and 180 min, blood (60 μL) was collected from a tail vein of each rat and mixed with an equal volume of 2 mg/mL $Na_2$-EDTA. The sample was added to a scintillation solution, and the radioactivity was measured in a liquid scintillation counter.

Figure 6:
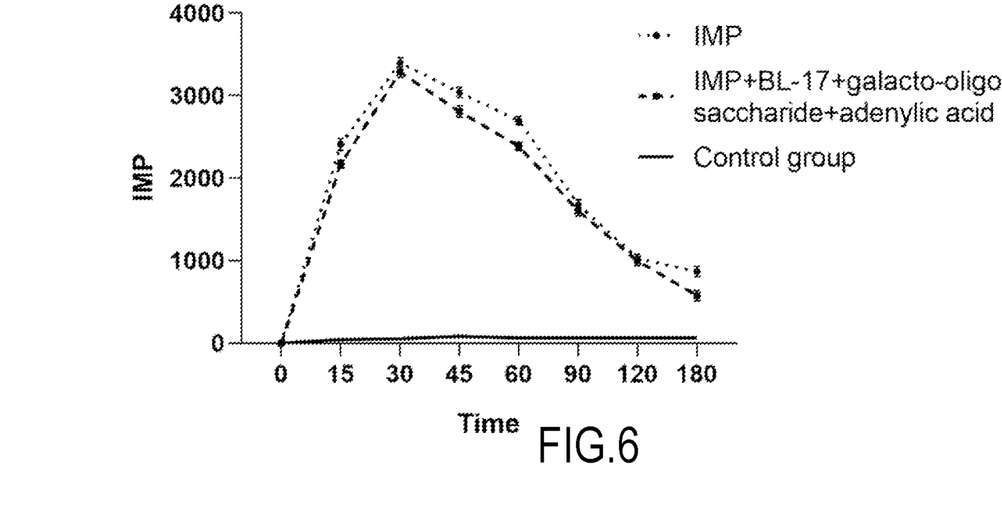
FIG. 6 shows the effect of the combination of the present disclosure on the intestinal absorption of IMP in rats.
Figure 7:
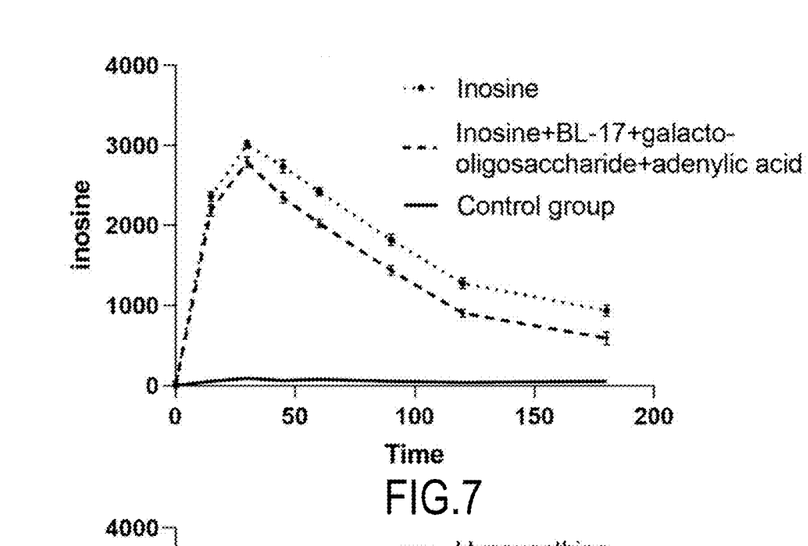
FIG. 7 shows the effect of the combination of the present disclosure on the intestinal absorption of inosine in rats.
Figure 8:
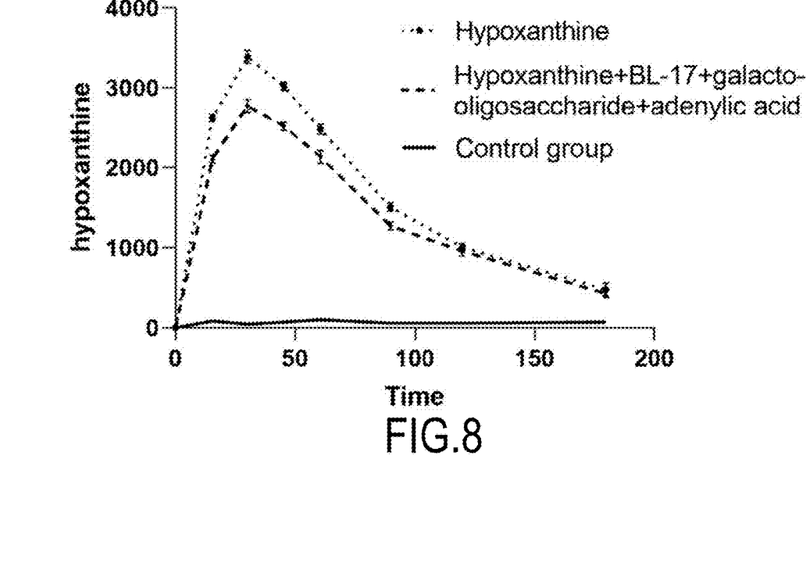
FIG. 8 shows the effect of the combination of the present disclosure on the intestinal absorption of hypoxanthine in rats.

5.2. An Experiment of the Combination to Reduce the Intestinal Absorption of Purines in Rats Rats were administered with labeled purines ($^{14}$C-inosinic acid (i.e. $^{14}$C-IMP), $^{14}$C-inosine, or $^{14}$C-hypoxanthine) and the combination, and then at different time points, radioactive purine contents in blood of rats were determined. Results are shown in FIG. 6, FIG. 7, and FIG. 8. At 45 min, 60 min, and 180 min after administration, the radioactivities in blood of rats administered with $^{14}$C-IMP and the combination are significantly lower than radioactivities in blood of rats administered with $^{14}$C-IMP alone. Similarly, at 30 min, 45 min, 60 min, 90 min, and 180 min after administration, radioactivities in blood of rats administered with $^{14}$C-inosine and the combination are significantly lower than radioactivities in blood of rats administered with $^{14}$C-inosine alone, and at 15 min, 30 min, 45 min, 60 min, and 90 min, radioactivities in blood of rats administered with $^{14}$C-hypoxanthine and the combination are significantly lower than radioactivities in blood of rats administered with $^{14}$C-hypoxanthine alone.

The combination contains a small amount of inosine, and the *Lactiplantibacillus plantarum* strain BL-17 can reduce the absorption of inosinic acid in rats through the direct uptake of inosine in the combination. The results observed with regard to inosine may be due to the fact that inosine is bound by the *Lactiplantibacillus plantarum* strain BL-17 and subsequently degraded to hypoxanthine which is less absorbed than inosine. The results observed with regard to hypoxanthine may be due to the fact that hypoxanthine is absorbed by the *Lactiplantibacillus plantarum* strain BL-17, and is absorbed at low levels in the intestinal tract. Due to the degradation of nucleosides and the absorption of purines by the *Lactiplantibacillus plantarum* strain BL-17, the intestinal absorption of purines is reduced. In addition, the effectiveness of nucleotides and nucleosides may be reduced because nucleotides and nucleosides are easily absorbed in the intestinal tract. As a functional oligosaccharide, the galacto-oligosaccharide can serve as a rich nutrient source for the *Lactiplantibacillus plantarum* strain BL-17 to promote the activity of the *Lactiplantibacillus plantarum* strain BL-17, enhancing the competitiveness of the *Lactiplantibacillus plantarum* strain BL-17 in an organism. The adenylic acid in the combination can promote the growth of the *Lactiplantibacillus plantarum* strain BL-17, thereby promoting the absorption of exogenous adenylic acid, adenosine, and adenine by the *Lactiplantibacillus plantarum* strain BL-17 and reducing the intestinal absorption of these purines in rats. The combination of the *Lactiplantibacillus plantarum* strain BL-17 with the galacto-oligosaccharide and the adenylic acid can attenuate the intestinal absorption of inosine and inosine-related purine compounds, and adenosine and adenosine-related purine compounds. The reduction of intestinal absorption of food-derived purines is important for maintaining a normal serum uric acid level. The combination of the *Lactiplantibacillus plantarum* strain BL-17 with the galacto-oligosaccharide and the adenylic acid may contribute to the health of patients with a high blood uric acid level and hyperuricemia.

The above are merely preferred embodiments of the present disclosure. It should be noted that a person of ordinary skill in the art may further make several improvements and modifications without departing from the principle of the present disclosure, but such improvements and modifications should be deemed as falling into the protection scope of the present disclosure.

What is claimed is:

1. A method of preparing a combination for alleviating hyperuricemia, wherein the combination comprises a *Lactiplantibacillus plantarum* strain BL-17 at a viable bacterial cell concentration of higher than or equal to $1\times10^6$ CFU/mL or higher than or equal to $1\times10^6$ CFU/g, 0.01 wt % galacto-oligosaccharide, and 0.01 wt % adenylic acid in a 100 g/L sterilized skimmed milk aqueous solution, and the *Lactiplantibacillus plantarum* strain BL-17 is deposited in China Center for Type Culture Collection (CCTCC), Wuhan on Oct. 19, 2022, with an accession number of CCTCC NO: M20221596;

wherein the preparation method comprises the following steps:

step 1, streaking the *Lactiplantibacillus plantarum* strain BL-17 on an MRS solid medium on a plate, picking a single colony for Gram staining, and after a single pure colony of the *Lactiplantibacillus plantarum* strain BL-17 is observed microscopically, subculturing the *Lactiplantibacillus plantarum* strain BL-17 twice in an MRS liquid medium to ensure the *Lactiplantibacillus plantarum* strain BL-17 is viable, to obtain an MRS liquid culture comprising the *Lactiplantibacillus plantarum* strain BL-17, and mixing 50% (v/v) glycerin aqueous solution and the MRS liquid culture in a volume ratio of 2:3 to obtain a resulting mixture, and storing the resulting mixture at −80° C. for later use;

step 2, inoculating the cryopreserved *Lactiplantibacillus plantarum* strain BL-17 into 5 mL of the MRS liquid medium at an inoculum size of 4% to obtain a mixture, incubating the mixture at 37° C. for 20 hours, followed by subculturing the cryopreserved *Lactiplantibacillus plantarum* strain BL-17 for two passages to obtain an MRS liquid culture comprising a *Lactiplantibacillus plantarum* strain BL-17 at passage 2; and centrifuging the MRS liquid culture comprising the *Lactiplantibacillus plantarum* strain BL-17 at passage 2 at 4° C. and 6,000 r/min for 5 min to obtain a bacterial pellet, collecting the bacterial pellet, washing the bacterial pellet twice with sterile normal saline to obtain a washed bacterial pellet, and collecting the washed bacterial pellet for subsequent preparation of a bacterial suspension; and step 3, resuspending the washed bacterial pellet in the 100 g/L sterilized skimmed milk aqueous solution and performing colony counting by a serial dilution and spread plate method to prepare a bacterial suspension with a concentration of $4.0\times10^9$ CFU/mL; and adding the galacto-oligosaccharide and the adenylic acid to the bacterial suspension contents such that the galacto-oligosaccharide and the adenylic acid are each at a concentration of 0.1 mg/mL; wherein the combination is capable of attenuating an intestinal absorption of an inosine and inosine-related purine compounds, and an adenosine and adenosine-related purine compounds.

2. A method for preventing and/or treating and alleviating hyperuricemia or preventing and/or treating gout, comprising administering to a subject a drug comprising a combination in an effective amount, wherein the combination comprises a *Lactiplantibacillus plantarum* strain BL-17 at a viable bacterial cell concentration of higher than or equal to $1\times10^6$ CFU/mL or higher than or equal to $1\times10^6$ CFU/g, 0.01 wt % galacto-oligosaccharide, and 0.01 wt % adenylic acid in a 100 g/L sterilized skimmed milk aqueous solution, and the *Lactiplantibacillus plantarum* strain BL-17 is deposited in China Center for Type Culture Collection (CCTCC), Wuhan on Oct. 19, 2022, with an accession number of CCTCC NO: M20221596; and the combination is capable of attenuating an intestinal absorption of an inosine and inosine-related purine compounds, and an adenosine and adenosine-related purine compounds.

3. A fermented food, comprising a combination, wherein the combination comprises a *Lactiplantibacillus plantarum* strain BL-17 at a viable bacterial cell concentration of higher than or equal to $1\times10^6$ CFU/mL or higher than or equal to $1\times10^6$ CFU/g, 0.01 wt % galacto-oligosaccharide, and 0.01 wt % adenylic acid in a 100 g/L sterilized skimmed milk aqueous solution, and the *Lactiplantibacillus plantarum* strain BL-17 is deposited in China Center for Type Culture Collection (CCTCC), Wuhan on Oct. 19, 2022, with an accession number of CCTCC NO: M20221596; and the combination is capable of attenuating an intestinal absorption of an inosine and inosine-related purine compounds, and an adenosine and adenosine-related purine compounds.

* * * * *